(12) United States Patent
Venkatesh et al.

(10) Patent No.: US 6,517,871 B1
(45) Date of Patent: Feb. 11, 2003

(54) BIOENHANCED FORMULATIONS COMPRISING EPROSARTAN IN ORAL SOLID DOSAGE FORM

(75) Inventors: Gopadi M. Venkatesh, Troy, MI (US); Manga R. Gudipati, Hatfield, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/743,946

(22) PCT Filed: Jul. 20, 1999

(86) PCT No.: PCT/US99/12396
§ 371 (c)(1),
(2), (4) Date: May 23, 2001

(87) PCT Pub. No.: WO00/04862
PCT Pub. Date: Feb. 3, 2000

Related U.S. Application Data

(60) Provisional application No. 60/093,418, filed on Jul. 20, 1998.

(51) Int. Cl.[7] ............ A61K 9/14; A61K 91/54; A61K 9/26; A61K 31/44; A61K 9/20

(52) U.S. Cl. .......... 424/489; 424/451; 424/457; 424/464; 424/468; 424/470; 514/341

(58) Field of Search .......... 424/489, 451, 424/457, 464, 468, 470; 514/341

(56) References Cited

U.S. PATENT DOCUMENTS

| | | | | |
|---|---|---|---|---|
| 5,185,351 A | * | 2/1993 | Finkelstein et al. | 514/341 |
| 5,795,909 A | * | 8/1998 | Shashousa et al. | 514/449 |
| 5,968,978 A | * | 10/1999 | Kleemann et al. | 514/524 |
| 5,985,915 A | | 11/1999 | Frangin et al. | |

* cited by examiner

Primary Examiner—Thurman K. Page
Assistant Examiner—Blessing Fubara
(74) Attorney, Agent, or Firm—Mary E. McCarthy; Charles M. Kinzig

(57) ABSTRACT

This invention relates to bioenhanced formulations comprising eprosartan or eprosartan mesylate in the amorphous form, a process for its production, compositions containing the compound and methods of using the compound to block angiotensin II receptors and to treat hypertension, congestive heart failure and renal failure.

42 Claims, 3 Drawing Sheets

BIOENHANCED FORMULATIONS COMPRISING EPROSARTAN IN ORAL SOLID DOSAGE FORM

The application is a 371 of PCT/US99/12396 filed Jul. 20, 1999 which claims benefit of Ser. No. 60/093,418 filed Jul. 20, 1998.

FIELD OF THE INVENTION

This invention relates to a phamaceutically active compound, bioenhanced formulations of eprosartan or eprosartan mesylate, processes for manufacturing the compound and these formulations and methods of using the bioenhanced formulations of eprosartan in the treatment of certain disease states in mammals, in particular man. Most specifically, the present invention relates to the use of eprosartan or eprosartan mesylate in the production of bioenhanced immediate and modified (both sustained and targeted) release oral solid dosage forms (tablet or capsule formulations) to block angiotensin II (AII) receptors and to treat hypertension, congestive heart failure and renal failure.

BACKGROUND OF THE INVENTION

The compound (E)-α-[2-n-butyl-1-[(4-carboxyphenyl)methyl]-1H-imidazol-5-yl]methylene-2-thiophenepropionic acid is known by the name eprosartan and is the subject of U.S. Pat. No. 5,185,351 (the '351 patent), issued Feb. 9, 1993. This patent discloses a process for making the anhydrous form of (E)-α-[2-n-butyl-1-(4-carboxyphenyl)methyl]-1H-imidazol-5-yl]methylene-2-thiophenepropionic acid and its methanesulfonate salt (eprosartan mesylate). Additionally, the '351 patent discloses conventional techniques for formulating (E)-α-[2-n-butyl-1-[(4-carboxyphenyl)methyl]-1H-imidazol-5-yl]methylene-2-thiophenepropionic acid. This compound is claimed to have utility in blocking angiotensin II receptors and to be useful in the treatment of hypertension, congestive heart failure and renal failure.

Because the variable and mean absolute bioavailability of eprosartan is approximately 13%, doses as high as 800 mg per day may be required for an effective treatment of hypertension, congestive heart failure and renal failure. Additionally, since the commercial form of the drug is as its mesylate, which becomes dihydrated during the formulation process, high dose tablets (e.g., 600 mg tablets weigh 1,200.0 mg) may be difficult to swallow. Therefore, there is a need for a formualtion that enhances the bioavailabiltiy of eprosartan.

Surprisingly, it has been found that eprosartan dissolved in ammonium hydroxide in the presence of poly(vinylpyrrolidone) (PVP) does not crystallize when spray dried or spray granulated using a fluid bed granulator. The drug substance in this spray dried or fluid bed granulated material is predominately in the amorphous form and, thus, is significantly more soluble in water, as well as body fluids. Consequently, the formulation containing the drug substance predominately in the amorphous form has been found to exhibit significantly greater bioavailability relative to the tablets of the current commercial formulation. Also, the present invention has resulted in a significant reduction in tablet size and may result in a significant increase in patient compliance. This is particularly important when formulating eprosartan or its mesylate salt for therapeutic use.

SUMMARY OF THE INVENTION

The present invention provides the amorphous ammonium salt of eprosartan. This form of eprosartan is prepared by dissolving eprosartan or eprosartan mesylate in ammonium hydroxide in the presence of a crystallization inhibitor.

Another aspect of the invention provides bioenhanced oral solid dosage forms of eprosartan, (E)-α-[2-n-butyl-1-[(4-carboxyphenyl)methyl]-1H-imidazol-5-yl]methylene-2-thiophenepropionic acid, or its any of its salt forms, in particular the monomethanesulfonate salt form, for the treatment of diseases in which blockade of angiotensin II receptors is indicated, for example, in the treatment of hypertension, congestive heart failure and renal failure. The present invention also provides a process for preparing bioenhanced capsule or tablet formulations of eprosartan or eprosatan mesylate by dissolving the anhydrous form of the drug substance in ammonium hydroxide in the presence of a pharmaceutically acceptable crystallization inhibitor, such as polyvinylpyrrolidone (PVP), and spray drying or granulating in a fluid bed granulator. These spray dried/fluid bed granules are blended with additional pharmaceutically acceptable to produce immediate release or modified (sustained or targeted) release oral solid dosage forms (capsules and tablets).

BRIEF DESCRIPTION OF THE FIGURES

The anhydrous forms of eprosartan and eprosartan mesylate exhibit a single thermal event, a melting endotherm at about 269° C. and 252° C., respectively. No significant weight loss prior to melting is observed in its TGA (thermogravimetric analysis), suggesting that neither of these compounds contains significant quantities of surface adsorbed water and/or residual solvents. The powder X-ray diffraction (XRD) patterns of the anhydrous form of eprosartan, eprosartan mesylate, spray dried eprosartan and spray dried eprosartan mesylate are presented in FIG. 1. The powder X-ray diffraction pattern of eprosartan exhibits characteristic diffraction lines corresponding to 2θ values of 8.15, 9.74, 14.20, 16.09, 17.09, 19.99, 20.71, 21.81, 22.38, 24.49, 26.84 and 31.39 degrees, while the XRD of eprosartan mesylate exhibits characteristic diffraction lines corresponding to 2θ values of 7.15, 13.90, 14.35, 18.30, 18.90, 20.10, 20.45, 21.00, 22.20, 24.35, 28.95 and 34.20 degrees. The spray dried formulations containing granules of eprosartan or eprosartan mesylate dissolved in ammonium hydroxide in the presence of PVP [Povidone (K-15/18)] exhibit a halo indicating that the formulations contain the drug substance predominately in the amorphous form. The pH-solubility profiles of the drug substances and their formulations are presented in FIG. 2. It is clear from these profiles that the formulations containing the spray dried granulations of eprosartan or eprosartan mesylate exhibit significantly higher solubilities and faster dissolution in water, as well as in gastrointestinal fluids, than their crystalline counterparts. The relative bioavailability data in dogs for the spray dried eprosartann formulation suggest that the mean $AUC_{(0-12)}$ and Cmax values increased 36% and 115%, respectively, when compared to the commercial eprosartan mesylate granules.

DETAILED DESCRIPTION OF THE INVENTION (E)-α-[2-n-Butyl-1-[(4-carboxyphenyl)methyl]-1H-imidazol-5-yl]methylene-2-thiophenepropionic acid (eprosartan) is known to exist in an anhydrous form. The commercial form of eprosartan is as its methanesulfonic acid salt and it has the following structure:

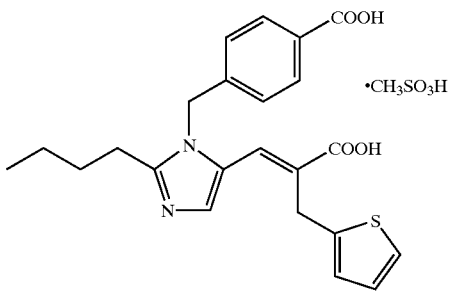

Figure 1A:
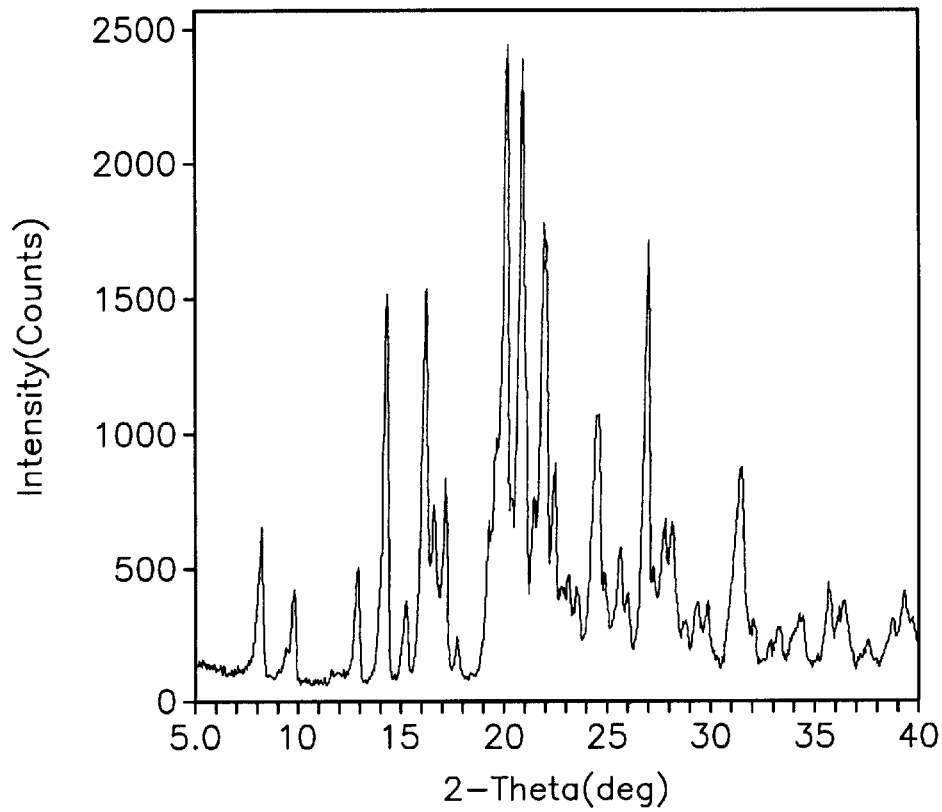
Figure 1B:
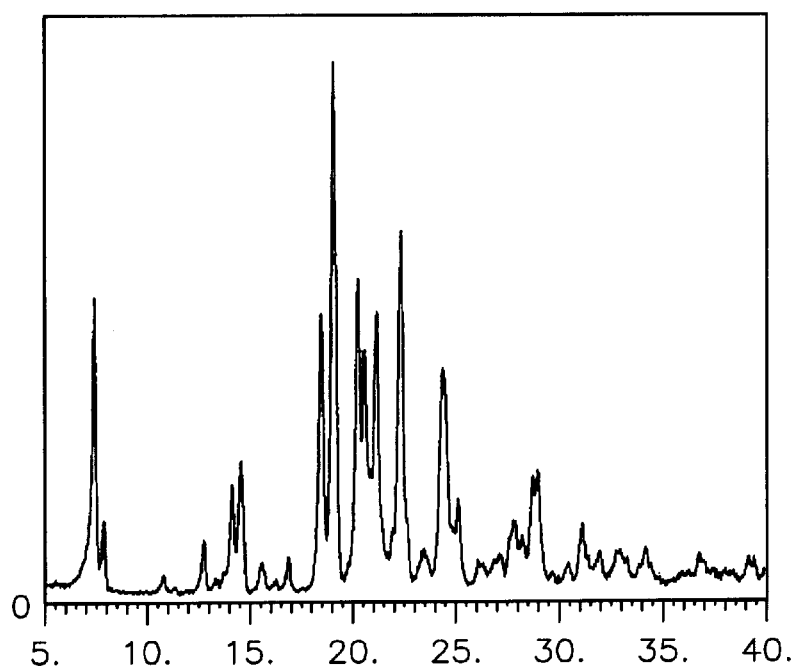
Figure 1C:
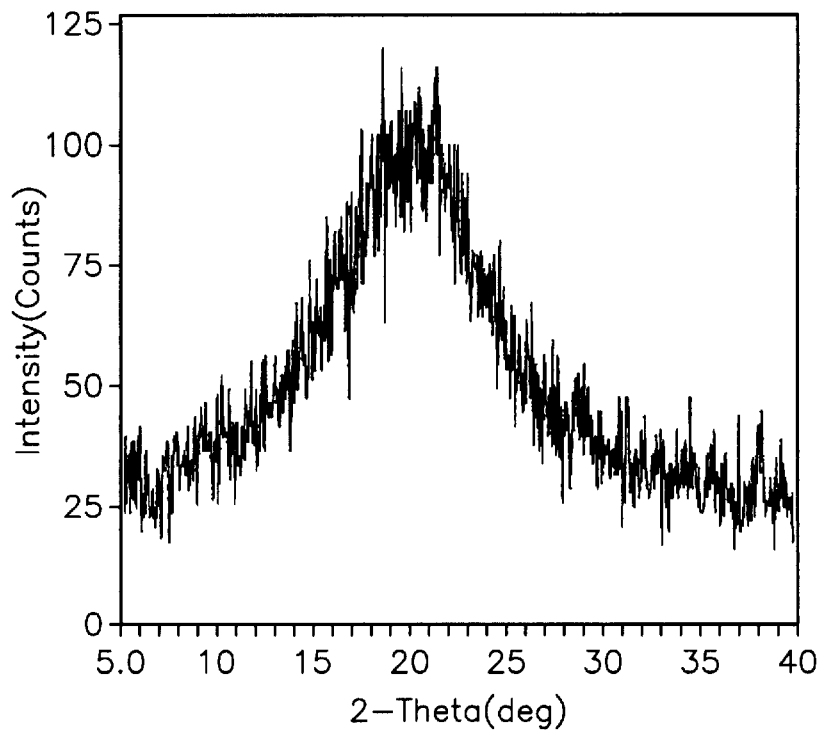
Figure 1D:
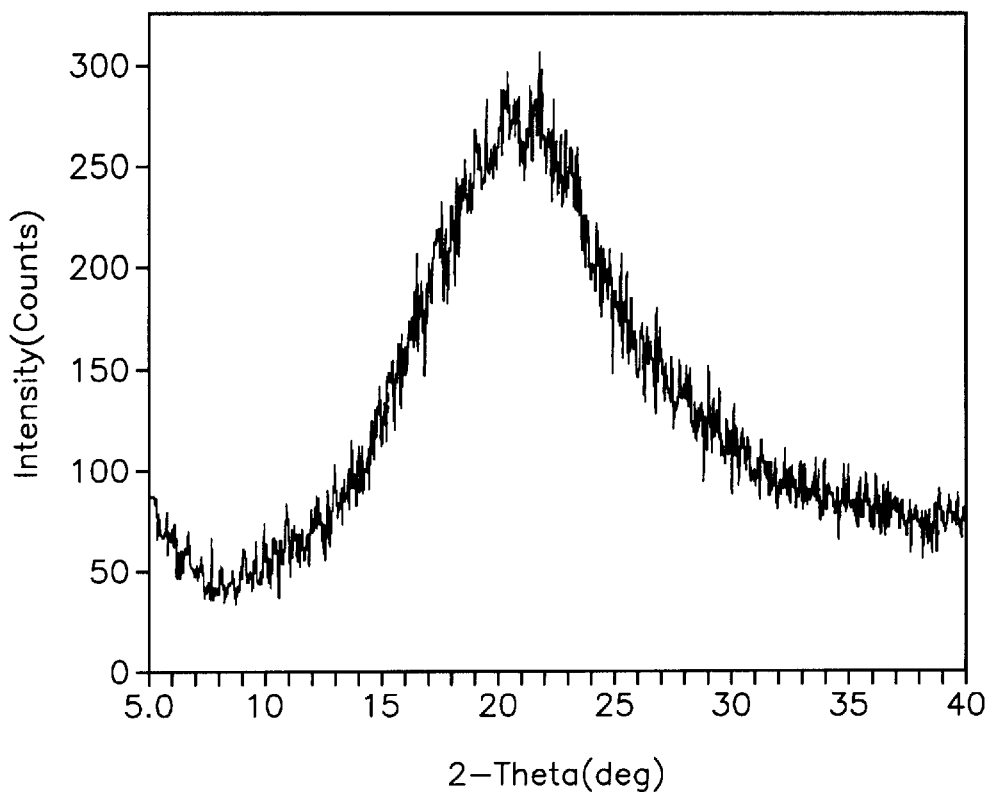
Figure 2:
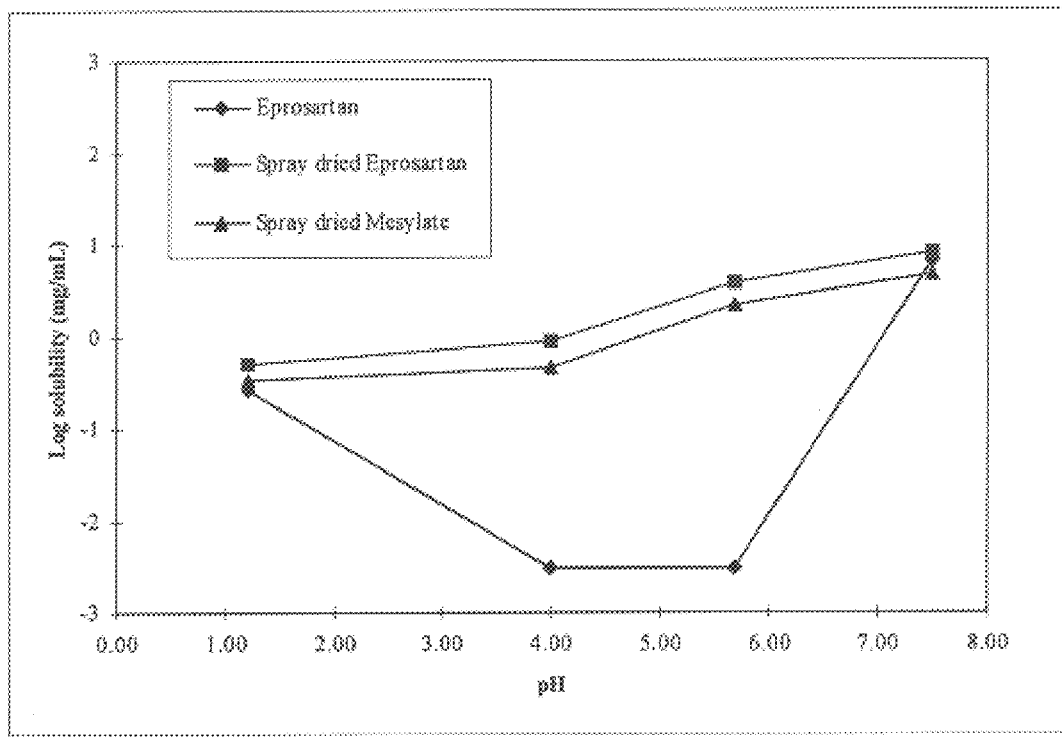

Eprosartan and eprosartan mesylate are claimed in U.S. Pat. No. 5,185,351. Reference should be made to said patent for its full disclosure, the entire disclosure of which is incorporated herein by reference.

The present invention provides a novel form of eprosartan, which is the amorphous ammonium salt form of eprosartan. This form of eprosartan is prepared by dissolving eprosartan or eprosartan mesylate in ammonium hydroxide in the presence of a crystallization inhibitor. Preferably, the crystallization inhibitor used in this process is polyvinylpyrrolidone (PVP).

Suitably, eprosartan or eprosartan mesylate are granulated predominately in amorphous form by dissolving the drug substance in ammonium hydroxide in the presence of a crystallization inhibitor, such as PVP, and optionally one or more pharmaceutically acceptable excipients, and then spray drying said solution or granulating said solution in a fluid bed granulator.

Preferably, a bioenhanced formulation of eprosartan or eprosartan mesylate is prepared by:
 (i) dissolving eprosartan or eprosartan mesylate in ammonium hydroxide in the presence of a crystallization inhibitor and optionally one or more pharmaceutically acceptable excipients;
 (ii) spray-drying the above solution, or granulating a mixture of pharmaceutical excipients and the above solution followed by drying in a fluid bed granulator; and
 (iii) filling into capsules or compressing into tablets the dried granulation, after additional blending with pharmaceutical excipients.

Suitably, the present invention provides a bioenhanced formulation of the amorphous ammonium salt of eprosartan and a pharmaceutically acceptable carrier. This formulation may be produce as an immediate release or modified (sustained or targeted) release oral solid dosage form (capsule or tablet).

As used herein, amorphous means a solid having no real or apparent crystalline form. By the term "predominately in amorphous form" is meant that the drug substance is mostly (greater than 50%) in amorphous form. Preferably, the drug substance is present in greater than 70% amorphous form. Most preferably, the drug substance is present in greater than 80% amorphous form.

As used herein, the term "crystallization inhibitor" means an agent that prevents a solid from taking on crystalline form.

As used herein, by sustained release is meant any formulation that achieves slow release of drug over an extended period of time. In the sustained release formulations of the instant invention, a portion of the eprosartan in the formulation is made available as a priming dose and the remainder is released in a sustained fashion. An example of a sustained release system is a matrix formulation.

By targeted release is meant any formulation having an enteric coat or a sustained release coat where timed release is achieved by a barrier coating.

As used herein, granulation means a solid containing the drug substance mixed with pharmaceutically acceptable carriers or excipients.

Eprosartan is an amphiphilic molecule containing two acidic (allylic carboxylic acid and phenylic carboxylic acid) and one basic (imidazole) functional groups. At lower pH (below 2) the imidazole nitrogen will be protonated (form ii). As the pH increases, the allylic carboxylic group will be deprotonated (form iii). Estimated $pK_a$ of the allylic carboxilic group is 2.9. As the pH increases further, the phenylic carboxylic group will be deprotonated (form iv) followed by the deprotonation of the protonated imidazole group (form v). The estimated $pK_a$ of the phenylic carboxylic group is 5.9 and that of imidazole group is 6.8. According to the pH-partitioning theory of absorption, only the unionized species (form ii) or the ion-neutral species (form iii) will be absorbed by passive diffusion. Human clinical studies indicate (E)-α-[2-n-butyl-1-[(4-carboxy phenyl)methyl]-1H-imidazol-5-yl]methylene-2-thiophenepropionic acid or its monomethanesulfonate (mesylate) salt to be safe and well tolerated, even up to doses of 800 mg per day. The time to maximum concentration is between 1 to 2.5 hours in fasted state and 2.5–4 hours in fed state. (E)-α-[2-n-Butyl-1-[(4-carboxyphenyl)methyl]-1H-imidazol-5-yl]methylene-2-thiophenepropionic acid monomethanesulfonate exhibits low and variable bioavailability with a mean absolute bioavailability of approximately 13%. Because the variable and mean absolute bioavailability of eprosartan is approximately 13%, doses as high as 800 mg per day may be required for an effective treatment of hypertension, congestive heart failure and renal failure. Additionally, since the commercial form of the drug is as its mesylate, which becomes dihydrated during the formulation process, high dose tablets (e.g., 600 mg tablets weigh 1,200.0 mg) may be difficult to swallow.

It has been found that the bioavailability of the spray dried material containing the free base or the mesylate salt in the amorphous form is 2–3 fold higher due to its significantly higher solubility and faster dissolution rate when compared to the corresponding crystalline free base or mesylate salt. Consequently, lower strength tablets are needed for effective treatment of hypertension, congestive heart failure and renal failure, resulting in lower cost of goods and hence, significantly improved patient compliance.

In accordance with the present invention, it has been found that stable bioenhanced tablet formulations containing (E)-α-[-2-n-butyl-1-[(4-carboxyphenyl)methyl]-1H-imidazol-5-yl]methylene-2-thiophenepropionic acid or its mesylate salt in the amorphous form are produced by dissolving the free base or mesylate salt in ammonium hydroxide in the presence of a crystallization inhibitor, such as PVP, and spray drying or granulating in a fluid bed granulator. The spray dried or fluid bed granulated material are blended with pharmaceutically acceptable carriers or excipients including binders, diluents, lubricants and disintegrants, and filled into capsules or compressed into tablets for immediate release or processed into matrix based or film coated dosage forms (beads, pellets or tablets) intended for modified or targeted release. Any combination of pharmaceutically acceptable carriers or excipients, e.g. diluents, fillers, binders and disintegrants, in desired proportions may be utilized with the spray dryedg or fluid bed granulated drug substance and immediate or modified release dosage forms of the present invention. The carriers or excipients commonly used in pharmaceutical industry are well described in the literature [refer to the Handbook of Pharmaceutical Excipients, A. Wade and P. J. Weller (Editors), American Pharmaceutical Association (1994)]. Pharmaceutically acceptable crystallization inhibitors include poly(vinyl pyrrolidone) and urea. Fillers and diluents include, but are not limited to, the following: lactose (hydrous as well as anhydrous), starch [unmodified (corn starch) or modified (for example, Starch 1500 available from Colorcon)], mannitol, sorbitol, cellulose, inorganic sulfates and phosphates. Disintegrants include, but are not limited to, the following: sodium starch glycolate, sodium carmellose and crosslinked polyvinyl pyrrolidone, and binders include, but are not limited to, the following: gelatin, corn starch, modified starch (Starch 1551, pregelatinized starch), hydroxypropyl methyl cellulose (HPMC), hydroxypropyl cellulose (HPC), sodium carboxy methyl cellulose, alginic acid, acacia and amino acids such as glycine, L-arginine, etc. Examples of excipients suitable for modified release applications include, but are not limited to, the following: high molecular weight HPMCs, polymethacrylate polymers known as Eudragit, polyethylene oxide, Polyox® (Union Carbide Corporation), modified ethyl cellulose, Surelease® (Colorcon), crosslinked acrylic acid polymers, Carbopol® (BF Goodrich Speciality Chemicals) and waxy materials, such as glyceryl behenate (Compritol®), glyceryl palmitostearate (Precirol®), and Gelucires® [all from Gattefosse s.a, France] and carnauba wax.

Preferably, the pharmaceutically acceptable excipients used as crystallization inhibitor and bulking agents during the spray drying/granulation process of this invention are lactose, mannitol, Povidone (PVP), sucrose, sodium starch glycolate, and microcrystalline cellulose to be incorporated in stable oral solid dosage forms of eprosartan by blending with additional excipients in desired proportions. More preferably, the excipients used as crystallization inhibitor and bulking agents during the spray drying/granulation process are mannitol/lactose, microcrystalline cellulose, sucrose, sodium starch glycolate and Povidone (PVP). Most preferably, the excipients used as crystallization inhibitor and bulking agents during the spray drying/granulation process are lactose/mannitol, microcrystalline cellulose and Povidone.

Preferably, the crystallization inhibitor and bulking agents used in the spray drying/granulation process are present in 2–80% on a weight for weight basis. Most preferably, the crystallization inhibitor and bulking agent(s) may be present at as low as 5–50% on a weight for weight basis in order to produce spray dried materials/granulations.

The process for preparing the solid dosage forms in accordance with the present invention may be carried out using a combination of a blender/stirrer, a spray dryer or a fluid bed granulator, a cummunuting mill, sieving equipment, a powder blender, a capsule filling machine or a tableting machine. Optionally, the spray dried material may be processed using a rotogranulator to produce spherical granules which may polymer film coated to impart modified release properties. Tablets of the spray dried/fluid bed granules may be optionally polymer film coated to produce delayed, sustained, or targeted release dosage forms.

Thus, the present invention provides a pharmaceutical composition which comprises (E)-α-[2-n-butyl-1-[(4-carboxyphenyl)methyl]-1H-imidazol-5-yl]methylene-2-thiophenepropionic acid or its mesylate salt mostly in the amorphous form. The pharmaceutical composition is adapted for oral administration. The composition is presented as a unit dose pharmaceutical composition containing from about 50 mg to about 1.0 g of (E)-α-[2-n-butyl-1-[(4-carboxyphenyl)methyl]-1H-imidazol-5-yl]methylene-2-thiophenepropionic acid or its salt, preferably from about 100 to about 400 mg. Such a composition is normally taken from 1 to 4 times daily, preferably from 1 to 2 times daily. The preferred unit dosage forms include tablets or capsules. The compositions of this invention may be formulated by conventional methods of admixture such as blending, filling and compressing. Suitable pharmaceutically acceptable excipients for use in this invention include diluents, fillers, binders and disintegrants.

(E)-α-[2-n-Butyl-1-[(4-carboxyphenyl)methyl]-1H-imidazol-5-yl]methylene-2-thiophenepropionic acid may be co-administered with other pharmaceutically active compounds, for example, in physical combination or by sequential administration. Conveniently, the compound of this invention and the other active compound are formulated in a pharmaceutical composition. Thus, this invention also relates to pharmaceutical compositions comprising (E)-α-[2-n-butyl-1-[(4-carboxyphenyl)methyl]-1H-imidazol-5-yl] methylene-2-thiophenepropionic acid, a pharmaceutically acceptable carrier, and a second pharmaceutically active compound selected from the group consisting of a diuretic, a calcium channel blocker, a β-adrenoceptor blocker, a renin inhibitor, and an angiotensin converting enzyme inhibitor. Examples of compounds which may be included in pharmaceutical compositions in combination with (E)-α-[2-n-butyl-1-[(4-carboxyphenyl)methyl]-1H-imidazol-5-yl] methylene-2-thiophenepropionic acid are diuretics, particularly a thiazide diuretic, such as hydrochlorothiazide, or a loop diuretic, such as furosemide, calcium channel blockers, particularly dihydropyridine antagonists, such as nifedipine, β-adrenoceptor blockers, such as propranolol, renin inhibitors, such as enalkinen, and angiotensin converting enzyme inhibitors, such as captopril or enalapril. Preferably, the pharmaceutical composition contains 200–400 mg of (E)-α-[2-n-butyl-1-[(4-carboxyphenyl)-methyl]-1H-imidazol-5-yl]methylene-2-thiophenepropionic acid in combination with 6.25–25 mg of hydrochlorothiazide.

No unacceptable toxicological effects are expected when (E)-α-[2-n-butyl-1-[(4-carboxyphenyl)methyl]-1H-imidazol-5-yl]methylene-2-thiophenepropionic acid is administered in accordance with the present invention.

(E)-α-[2-n-Butyl-1-[(4-carboxyphenyl)methyl]-1H-imidazol-5-yl]methylene-2-thiophenepropionic acid is useful for treating diseases in which blockade of the angiotensin II receptor would be beneficial. Preferably, this compound is used alone or in combination with said second pharmaceutically active compounds in the treatment of hypertension, congestive heart failure and renal failure. Additionally, (E)-α-[2-n-butyl-1-[(4-carboxy-phenyl)methyl]-1H-imidazol-5-yl]methylene-2-thiophenepropionic acid is of value in the treatment of left ventricular hypertrophy regression, diabetic nephropathy, diabetic retinopathy, mascular degeneration, haemorrhagic stroke, primary and secondary prevention of infarction, prevention of atheroma progression and the regression of atheroma, prevention of restinosis after angioplasty or bypass surgery, improving cognitive function, angina, glaucoma, and CNS disorders, such as anxiety.

The following examples are illustrative of the instant invention. These examples are not intended to limit the scope of this invention as defined hereinabove and as claimed hereinbelow.

In Examples 1–8, below, the term "internal granules" means the spray dried/fluid bed granulation obtained by dissolving eprosartan or its salt, poly(vinyl pyrrolidone) and optionally mannitol in ammonium hydroxide and spray drying using conventional spray drying equipment or spraying on to bulking agents in a fluid bed granulator.

EXAMPLES
Capsule Formulations

Example 1

80 parts of Eprosartan and 2.0 parts PVP (K-15/18) are dissolved in ammonium hydroxide in a mixer-stirrer. The solution is spray dried using a Yamato spray dryer. 60 parts of the spray dried material (internal granules) is blended with 39 parts of spray dried mannitol and 1 part magnesium stearate and filled into hard gelatin capsules using a capsule filling machine to produce 100 mg strength eprosartan capsules which rapidly dissolve when tested for dissolution using USP Apparatus 1 in simulated intestinal fluid (pH= 7.6).

Example 2

61.3 parts of Eprosartan mesylate, 23.0 parts of PVP (K-15/18), and 15.7 parts of mannitol are dissolved in ammonium hydroxide and the solution is spray dried using a Yamato spray dryer. The spray dried granulation is filled into hard gelatin capsules using a Minicap 50 capsule filling machine.

Immediate Release Tablet Formulations

Examples 3 & 4

61.3 parts of Eprosartan mesylate and 20.0 parts of PVP (K-15/18) are dissolved in ammonium hydroxide and the solution is sprayed on to a mixture of 10.7 parts of mannitol, 6 parts of microcrystalline cellulose (Avicel PH102) and 2 parts of crosslinked PVP (Crospovidone) in a fluid bed granulator. The dried granulation is milled to produce granules passing through a #30 mesh or appropriate size sieve. Compression mixes with ingredients as listed in Formulas 1 and 2 are prepared by blending and compressed into 300 mg tablets of hardness in the range of 7–10 kP using a tablet press.

| Ingredients (%) | Formula 1 | Formula 2 |
| --- | --- | --- |
| Internal granules | 89.3 | 89.3 |
| Avicel PH 102 | 8.0 | |
| Hydroxypropylmethyl cellulose Methocel E5 | — | 8.0 |
| Crospovidone, crosslinked PVP | 2.0 | 2.0 |
| Magnesium stearate | 0.7 | 0.7 |
| Total | 100.0 | 100.0 |

Tablets of Formulas 1 and 2 rapidly release the drug when tested for dissolution in simulated gastric fluid using USP Apparatus 1 (baskets@ 100 rpm).

Modified Release Tablet Formulations

Examples 5 & 6

Using the internal granulation produced as stated in Examples 3 and 4, compression mixes with ingredients as listed in Formulas 3 and 4 are prepared by blending and compressed into 300 mg tablets of hardness in the range of 7–10 kp using a tablet press.

| Ingredients (%) | Formula 4 | Formula 3 |
| --- | --- | --- |
| Internal granules | 82.3 | 82.3 |
| Avicel PH 102 | 7.0 | 7.0 |
| Hydroxypropylmethyl cellulose Methocel E4M | 10.0 | |
| Poly(vinylacetatephthalate) (PVAP) | | 10.0 |
| Magnesium stearate | 0.7 | 0.7 |
| Total | 100.0 | 100.0 |

Tablets of Formulas 3 and 4 take more than an hour to release 90% of the drug when identically tested for dissolution using USP Apparatus 1 (baskets@ 100 rpm) in simulated gastric and intestinal fluids, respectively.

If the rate of dissolution of the drug substance from the dosage form, following oral administration, is significantly faster than the rate of absorption, which is very likely in case of Formulas 2 to 6, then the extent of bioavailability may be significantly enhanced in comparison to that of the capsule formulation of Example 1.

Examples 7 and 8

61.3 parts of Eprosartan mesylate and 20.0 parts of PVP (K-15/18) are dissolved in ammonium hydroxide and the solution is sprayed on to a mixture of 10.7 parts of mannitol, 6 parts of microcrystalline cellulose (Avicel PH102) and 2 parts of crosslinked PVP (Crospovidone) in a fluid bed granulator. The dried granulation is milled to produce granules passing through a #30 mesh or appropriate size sieve. Compression mixes with ingredients as listed in Formulas 5 and 6 are prepared by blending and compressed into 300 mg tablets of hardness in the range of 7–10 kP using a tablet press.

| Ingredients (%) | Formula 5 | Formula 6 |
| --- | --- | --- |
| Internal granules | 89.3 | 79.3 |
| Avicel PH 102 | 8.0 | |
| L-Arginine | | 20.0 |
| Crospovidone, crosslinked PVP | 2.0 | |
| Magnesium stearate | 0.7 | 0.7 |
| Total | 100.0 | 100.0 |

Tablets of Formulas 5 and 6 are coated with an aqueous formulation of polyvinyl acetate phthalate to a weight of about 8%.

Film Coating

Tablets of Formulas 1 to 4 may be optionally provided with an aqueous film coating. Generally, these tablets are coated first with a polymer solution to form a clear film, and then coated with an aqueous polymer solution/suspension to form an opaque, white or colored film. This film coating does not have any effect on the disintegration of the tablet, and hence, the drug dissolution is not affected. In contrast, tablets of Formulas 5 and 6 may be first coated with an aqueous polymer solution to form a clear film (often called seal coat) and then with an aqueous solution/suspension of an enteric polymer such as Eudragit L30D, hydroxypropyl methylcellulose acetate phthalate (HPMCP), or cellulose acetate phthalate (CAP). The weight gains following seal coat and enteric coat are about 2–6% and 4–12% (most preferably 3–4% and 6–8%) respectively. The modified release tablets thus produced release <20% drug in the stomach following the oral administration and rapidly release the drug at higher pHs, depending on the polymer used (for e.g., at a pH >4.0 for PVAP, >5.0 for HPMCP and 5.5 for Eudragit), even though the drug solubility at these initiation pHs is negligible. The water imbibed into the tablets dissolves arginine creating a high pH environment in which Eprosartan dissolves. This high pH also dissolves the film coating, releasing the drug substance to the environment.

It is to be understood that the invention is not limited to the embodiments illustrated hereinabove and the right is reserved to the illustrated embodiments and all modifications coming within the scope of the following claims.

What is claimed is:

1. A compound which is the amorphous ammonium salt of eprosartan.

2. A granulation comprising eprosartan predominately in amorphous form.

3. A bioenhanced formulation comprising the amorphous ammonium salt of eprosartan and a pharmaceutically acceptable carrier.

4. A process for preparing the compound according to claim 1 wherein eprosartan or eprosartan mesylate is dissolved in ammonium hydroxide in the presence of a crystallization inhibitor.

5. The process of claim 4 wherein the crystallization inhibitor is poly(vinylpyrrolidone) [PVP].

6. A process for preparing the granulation according to claim 2 wherein eprosartan or eprosartan mesylate is dissolved in ammonium hydroxide in the presence of a crystallization inhibitor, and optionally one or more pharmaceutically acceptable excipients, and then is spray dryed or granulated in a fluid bed granulator.

7. The process of claim 6 wherein the crystallization inhibitor is PVP.

8. The process of claim 6 wherein the excipient is mannitol.

9. A process for preparing the formulation according to claim 3 which comprises:
 (i) dissolving eprosartan or eprosartan mesylate in ammonium hydroxide in the presence of a crystallization inhibitor and optionally one or more pharmaceutically acceptable excipients;
 (ii) spray-drying the above solution, or granulating a mixture of pharmaceutical excipients and the above solution followed by drying in a fluid bed granulator; and
 (iii) filling into capsules or compressing into tablets the dried granulation, after additional blending with pharmaceutical excipients.

10. The formulation according to claim 3 in a modified release solid dosage form.

11. A process for preparing the formulation according to claim 10 which comprises:
 (i) producing granules containing eprosartan in the amorphous form;
 (ii) blending said granules optionally with other pharmaceutically acceptable excipients to be compressed into a tablet; and
 (iii) coating said tablet with polymers which modify, delay or target the release of eprosartan.

12. The process according to claim 11 wherein the coating is an enteric polymer selected from the group consisting of polyvinyl acetate phthalate and modified polymethamethacrylate (Eudragit L30D).

13. A pharmaceutical composition comprising the compound according to claim 1 and a second pharmaceutically active compound selected from the group consisting of a diuretic, a calcium channel blocker, a β-adrenoceptor blocker, a renin inhibitor, and an angiotensin converting enzyme inhibitor.

14. The pharmaceutical composition according to claim 13 wherein the second pharmaceutically active compound is a diuretic.

15. The pharmaceutical composition according to claim 14 wherein the diuretic is hydrochlorothiazide.

16. The pharmaceutical composition according to claim 13 wherein the second pharmaceutically active compound is a loop diuretic.

17. The pharmaceutical composition according to claim 16 wherein the loop diuretic is furosemide.

18. The pharmaceutical composition according to claim 13 wherein the second pharmaceutically active compound is a calcium channel blocker.

19. The pharmaceutical composition according to claim 18 wherein the calcium channel blocker is nifedipine.

20. The pharmaceutical composition according to claim 13 wherein the second pharmaceutically active compound is a β-adrenoceptor blocker.

21. The pharmaceutical composition according to claim 20 wherein the β-adrenoceptor blocker is propranolol.

22. The pharmaceutical composition according to claim 13 wherein the second pharmaceutically active compound is an angiotensin converting enzyme inhibitor.

23. The pharmaceutical composition according to claim 20 wherein the angiotensin converting enzyme inhibitor is captopril or enalapril.

24. The pharmaceutical composition according to claim 13 wherein the second pharmaceutically active compound is a renin inhibitor.

25. The pharmaceutical composition according to claim 20 wherein the renin inhibitor is enalkinen.

26. A method of blocking angiotensin II receptors which comprises administering to a subject in need thereof an effective amount of the compound according to claim 1.

27. A method of treating hypertension which comprises administering to a subject in need thereof an effective amount of the compound according to claim 1.

28. A method of treating hypertension which comprises administering stepwise or in physical combination the compound according to claim 1 and a second pharmaceutically active compound selected from the group consisting of a diuretic, a calcium channel blocker, a β-adrenoceptor blocker, a renin inhibitor, and an angiotensin converting enzyme inhibitor.

29. The method according to claim 28 wherein the second pharmaceutically active compound is a diuretic.

30. The method according to claim 29 wherein the diuretic is hydrochlorothiazide.

31. The method according to claim 28 wherein the second pharmaceutically active compound is a loop diuretic.

32. The method of claim 31 wherein the loop diuretic is furosemide.

33. The method according to claim 28 wherein the second pharmaceutically active compound is a calcium channel blocker.

34. The method according to claim 33 wherein the calcium channel blocker is nifedipine.

35. The method according to claim 28 wherein the second pharmaceutically active compound is a β-adrenoceptor blocker.

36. The method according to claim 35 wherein the β-adrenoceptor blocker is propranolol.

37. The method according to claim 28 wherein the second pharmaceutically active compound is an angiotensin converting enzyme inhibitor.

38. The method according to claim 37 wherein the angiotensin converting enzyme inhibitor is captopril or enalapril.

39. The method according to claim 28 wherein the second pharmaceutically active compound is a renin inhibitor.

40. The method according to claim 39 wherein the renin inhibitor is enalkinen.

41. A method of treating congestive heart failure which comprises administering to a subject in need thereof an effective amount of the compound according to claim 1.

42. A method of treating renal failure which comprises administering to a subject in need thereof an effective amount of the compound according to claim 1.

\* \* \* \* \*